United States Patent
Gupta et al.

(10) Patent No.: US 6,370,480 B1
(45) Date of Patent: Apr. 9, 2002

(54) QUANTITATIVE ANALYSIS SYSTEM AND METHOD FOR CERTIFYING ULTRASOUND MEDICAL IMAGING EQUIPMENT

(75) Inventors: Rajiv Gupta, New York; Yibin Zheng, Rexford, both of NY (US); Christopher James Dailey, Sommerville, SC (US)

(73) Assignee: General Electric Company, Schenectady, NY (US)

( * ) Notice: Subject to any disclaimer, the term of this patent is extended or adjusted under 35 U.S.C. 154(b) by 0 days.

(21) Appl. No.: 09/316,011

(22) Filed: May 21, 1999

(51) Int. Cl.[7] .............................................. G01B 7/008
(52) U.S. Cl. ....................................... 702/39; 73/866.4
(58) Field of Search ........................... 702/39, 54, 159, 702/171, 71, 33, 35; 73/1.01, 1.82, 865.9, 618, 619, 640, 570, 620, 866.4, 865.6; 128/915, 916, 922, 923

(56) References Cited

U.S. PATENT DOCUMENTS

| | | | |
|---|---|---|---|
| 4,644,510 A | * 2/1987 | Fujii | 367/87 |
| 5,465,720 A | * 11/1995 | Kurzynski et al. | 128/660.01 |
| 5,560,242 A | * 10/1996 | Flax | 73/1 |
| 5,574,212 A | 11/1996 | Madsen et al. | |
| 5,600,574 A | * 2/1997 | Reitan | 702/185 |
| 5,656,763 A | * 8/1997 | Flax | 73/1.82 |
| 5,670,719 A | * 9/1997 | Madsen et al. | 73/619 |
| 5,689,443 A | 11/1997 | Ramanathan | |
| 5,827,942 A | 10/1998 | Madsen et al. | |

* cited by examiner

Primary Examiner—Marc S. Hoff
Assistant Examiner—Edward Raymond
(74) Attorney, Agent, or Firm—Jill M. Breedlove; Christian G. Cabou

(57) ABSTRACT

An analysis system and method provide for quantitatively evaluating image quality characteristics of an ultrasound imaging machine that evaluates at least one image representation of a standard phantom acquired by the image machine. The machine under test by comparing acquired parameters with prestored values, and returning a determined set of image quality indices, along with a single index representing an arithmetic combination of all other image quality indices, which indicate the accuracy of the test image relative to a "gold standard" that has been pre-established for the model of imaging machine under investigation. The system, which includes a computer-programmed set of instructions and data, optionally includes at least one standard phantom. The image quality indices, or metrics, quantitatively represent an evaluation of a test image using a set of relatively subjective criteria that include homogeneity, contrast, signal attenuation and penetration of depth, pin to background ratio in near and far-field, axial and lateral resolution, modulation transfer function, and geometric distortion, and axial and lateral linearity. These image quality indices are determined by specific algorithms and then combined to form an image health index. The image health index and the individual component indices are compared to a gold standard set of indices obtained from an equivalent imaging machine operating under optimum conditions and settings.

24 Claims, 13 Drawing Sheets

QUANTITATIVE ANALYSIS SYSTEM AND METHOD FOR CERTIFYING ULTRASOUND MEDICAL IMAGING EQUIPMENT

BACKGROUND OF THE INVENTION

The invention relates generally to the field of ultrasound imaging machines and particularly, to a quantitative analysis system and method for certifying ultrasound medical equipment. More particularly, the invention is related to the use of a quantitative analysis program for testing the resolution capabilities of such imaging machines using imaging phantoms as test objects and returning a set of indices indicating the condition of the imaging machine.

An ultrasound imaging machine is an electronic device including a signal transmission and detection apparatus for producing an ultrasound image. A medical ultrasound imaging machine is used for uninvasive in vivo visualization so that anatomical structures within a body of a patient are displayed and analyzed. Such a machine transmits sound waves of very high frequency (typically 2 MHZ to 10 MHZ) into the patient and then processes echoes reflected from structures in the patient's body. The purpose of the ultrasound imaging machine is to display and/or analyze the return echoes, which are the result of the phenomena of refraction, reflection, scattering absorption and dispersion of radio frequency ultrasonic pressure waves from a tissue medium in the patient's body. The images formed by the return echoes have a granular structure and are described as having a degree of texture or speckle. The ability of the ultrasound imaging machine to produce an image distinguishing a target object in a scanned volume, known as a slice, from the texture in the image produced from adjacent background material, is defined as imaging machine resolution, or image resolution. A target object distinguished from background structure is said to be resolved. A resolved image is typically stored in memory and on storage devices configured to optimize image storage. Resolved images are displayed for visual examination and analysis on a display device, such as a video monitor or a printer.

Image resolution represents a combination of both independent and inter-related factors, to be described in detail below, that contribute to faithful and repeatable reproduction of medical images. Faithful and repeatable image reproduction is a consequence of periodic testing and calibration of the ultrasonic scanning system. Periodic calibration is necessary because medical images are used as part of human diagnostic procedures. To ensure that this is done, in the United States, federal and state requirements have been established, and the American Institute of Ultrasound in Medicine (AIUM) Ultrasound Practice Accreditation Commission has developed guidelines for ultrasound practice accreditation. According to U.S. guidelines and government requirements, each health-care provider using an ultrasound machine must go through an accreditation process to ensure that the instrumentation used for diagnostic procedures meets established standards. Further, each health-care provider must periodically have ultrasound instrumentation serviced and calibrated regularly and must undergo image quality certification according to the manufacturer's specification.

For quality assurance, these guidelines recommend that routine testing and calibration be made with the use of ultrasound test objects known as "phantoms". A variety of types of commercially available phantoms are currently used for certifying the function of an ultrasonic machine, each emphasizing the evaluation of one or more test parameters.

The typical phantom includes a gel having a smooth texture, which mimics human tissue and emphasizes image nonuniformities and artifacts, making such spurious features easier to detect. Commercially available phantoms contain artificial "targets" embedded in the uniform background gel material, which mimic various entities found in the human body, including liver tissue, tumors and cysts. Commercially available phantoms also contain pin targets arranged at precisely defined orientations and distances from each other, and relative to the scanned slice. A pin is a very small, (compared to the resolution of the imaging machine) high reflectance object, that mimics an infinitely small point. Use of pins as targets determines the accuracy of reproduction of vertical and horizontal dimensions and distances. For example, a set of evenly spaced vertical pins and a separate set of evenly spaced horizontal pins are used to measure the horizontal and vertical linearity of an image.

Methods for evaluating the accuracy of an ultrasound image by utilizing a specific set of algorithms that evaluate performance parameters and which report the results for screen display are known in the art. For example, U.S. Pat. No. 5,689,443 discloses a system that stores information about the scanner, about expected performance standards, and the specifications of at least one phantom test object. Information about the phantom test object includes an image of the phantom test object and preset or prestored spatial measurements of features embedded within the phantom test object. The system processes a test image of the phantom test object and compares the results with the stored information about the actual phantom test object, to quantitatively determine the characteristics of the scanner. The system provides for 1) determination of scanner performance for a particular image, 2) calculations for reporting on all images of a test, and 3) storage and subsequent retrieval of previous measurements obtained by the same scanner for comparison and trend analysis. The user selects regions of the phantom test object and directs the system to employ algorithmic techniques to analyze only the selected region for a variety of image characteristics, for example, contrast, resolution and homogeneity.

While the system just described tests an ultrasound image machine by imaging a phantom test object, and provides for comparison of test results with prior results obtained by that same machine, the system does not compare the test results specifically with an optimum, or "gold standard", image of the phantom test object. Such an optimum, or "gold standard" image is defined as an image obtained by the same model image machine as being tested, wherein the machine is operating optimally according to manufacturer's specifications and under optimum conditions.

In addition, while the system of U.S. Pat. No. 5,689,443 quantifies certain image quality parameters, such as resolution, contrast, and homogeneity, the system does not provide a specific index for each parameter, such that the indices, both individually and in combination, provide a quantitative assessment of the image machine imaging capability. In particular, the system does not arithmetically combine the individual image quality indices to produce one collective index, which could be called an "Image Health Index". The system does not indicate to the user, in terms of these individual and collective image quality indices, how the current image test results compare with the above-defined "gold standard" image of the same test.

Further, the system of U.S. Pat. No. 5,689,443 does not automatically shift the test image representation until it is in registration with a comparison image representation obtained from storage or from an outside source, and then compare parameters determined from the two image representations.

While algorithms for isolating and analyzing phantom test objects are known in the art, and while some prior art algorithms attempt to quantify subjective image quality, there exists a need for a tool that utilizes known phantoms, in conjunction with a unique set of algorithms, that quantitatively evaluates a test image by using a comprehensive set of relatively subjective image quality criteria to generate a single indicator. Such a tool needs to examine these, and other criteria, in terms of several parameters derived from a test image and a "gold standard" image, and return a set of indices, along with a single index representing an arithmetic combination of all other image quality indices, which indicates the accuracy of the test image relative to the "gold standard" that has been pre-established for the model of imaging machine under investigation.

BRIEF SUMMARY OF THE INVENTION

In an exemplary embodiment of the invention, a system is provided for quantitatively evaluating image quality characteristics of an ultrasound imaging machine. The system includes a circuit controlled by a computer program and a standard phantom, wherein the computer program electronically evaluates at least one image representation of the standard phantom acquired by the image machine under test. Acquired parameters are compared with prestored values, and a determined set of image quality indices is returned, along with a single index representing an arithmetic combination of all other image quality indices. The image quality indices indicate the accuracy of the test image relative to a "gold standard" that has been pre-established for the model of imaging machine under investigation. The system, which includes a computer-programmed set of instructions and data, optionally includes at least one standard phantom. The present invention also is thought of as an ultrasound imaging machine quality analysis tool for use with a standard phantom.

The image quality indices, or metrics, quantitatively represent an evaluation of a test image on a set of relatively subjective criteria that generally are regarded as part of intuitive observations by the image machine user. Subjective image quality criteria generally relate to intuitive observations, such as poor contrast, and fuzzy image. These image quality indices include homogeneity, contrast, signal attenuation and penetration of depth, pin to background ratio in near and far-field, axial and lateral resolution, modulation transfer function, and geometric distortion, and axial and lateral linearity. According to the invention, these image quality indices are determined by specific algorithms and then combined to form an image health index. The image health index and the individual component indices are compared to a gold standard set of indices obtained from an equivalent imaging machine operating under optimum conditions and settings.

For each ultrasound imaging machine model, and for each clinically significant setting of the machine, a gold standard set of indices is previously acquired from a "standard" phantom. This commercially available standard phantom is specially built to allow image to image registration, i.e., alignment of multiple images acquired from the same target area, via a set of fiducial markers arranged for alignment purposes. In addition, a set of echoic structures and pins are embedded in the standard phantom to simulate a diverse set of imaging conditions such as scattering objects, near and far-field reflectors, etc. Because the approximate position and radii of these structures in the phantom is stored within the measurement system beforehand, the system places a set of regions of interest around the structures. The regions of interest are then finely registered between the test image and the standard image. After registration, the system determines the image quality indices for each region of interest. The same indices are also computed for the standard image. These two sets of indices are compared and from the standardized difference, a "similarity index" is computed.

The obtained image health index and the individual component indices are useful in 1) certification that an ultrasound machine is producing images of acceptable image quality, and is functioning properly, and 2) monitoring the condition of an installed machine and assisting in diagnosing a malfunction of the machine.

DETAILED DESCRIPTION OF THE INVENTION

Figure 1:
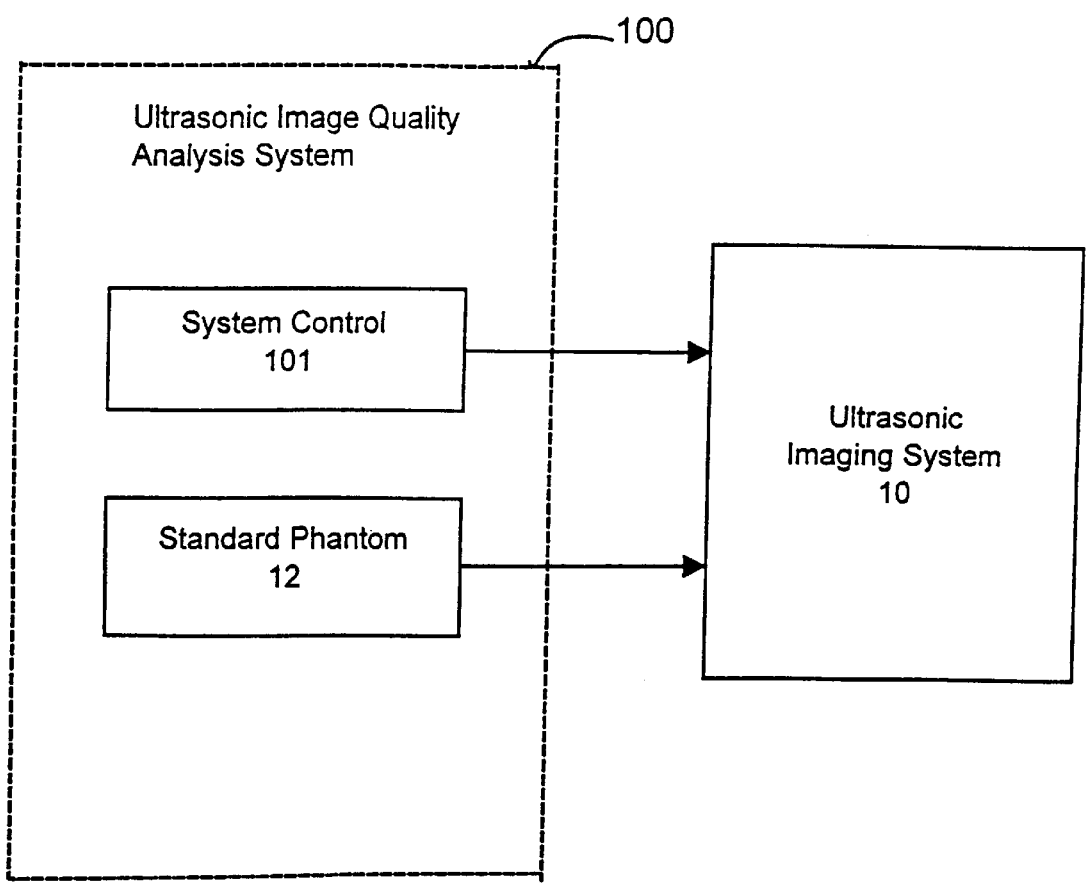
FIG. 1 is a simplified schematic of the ultrasound image machine image quality analysis system according to the present invention adapted to a known arrangement of an ultrasound imaging system.

FIG. 1, according to the present invention, is a simplified block diagram of showing an ultrasound imaging system 10 adapted to cooperate with the ultrasound image machine image quality analysis system 100 of the present invention. System 100 includes a system control program 101 and a standard phantom 12. The central function of the ultrasound image quality analysis system 100, according to the present invention, is to acquire an image representation of a standard phantom 12 by means of an ultrasound machine under test, compare that representation with representations of the same, or equivalent standard phantom 12 previously acquired under ideal conditions to be described, and output a series of indices indicative of the operational efficacy of the machine being tested.

Indices indicative of operational efficacy generally are calculated from brightness values and spatial separation of pixel elements comprising the image. A typical ultrasound image is a two dimensional image consisting of discrete pixel elements, each having a level of brightness relative to a "grayscale" value. The pixel elements are arranged in orthogonal rows and columns, and square or rectangular subset areas of such rows and columns are identified by the user as approximate regions of interest. Preferably, a commonly known graphical user interface is provided and commonly known graphical input techniques are used to communicate the selected region of interest to system control 101. A region of interest is variously characterized, for example, by calculating its mean and standard deviation grayscale value of pixels within the region, or by calculating contrasting grayscale values of adjacent component areas internal to a given region. Each of these methods will be described in more detail below, in connection with calculation of image quality indices.

Figure 2:
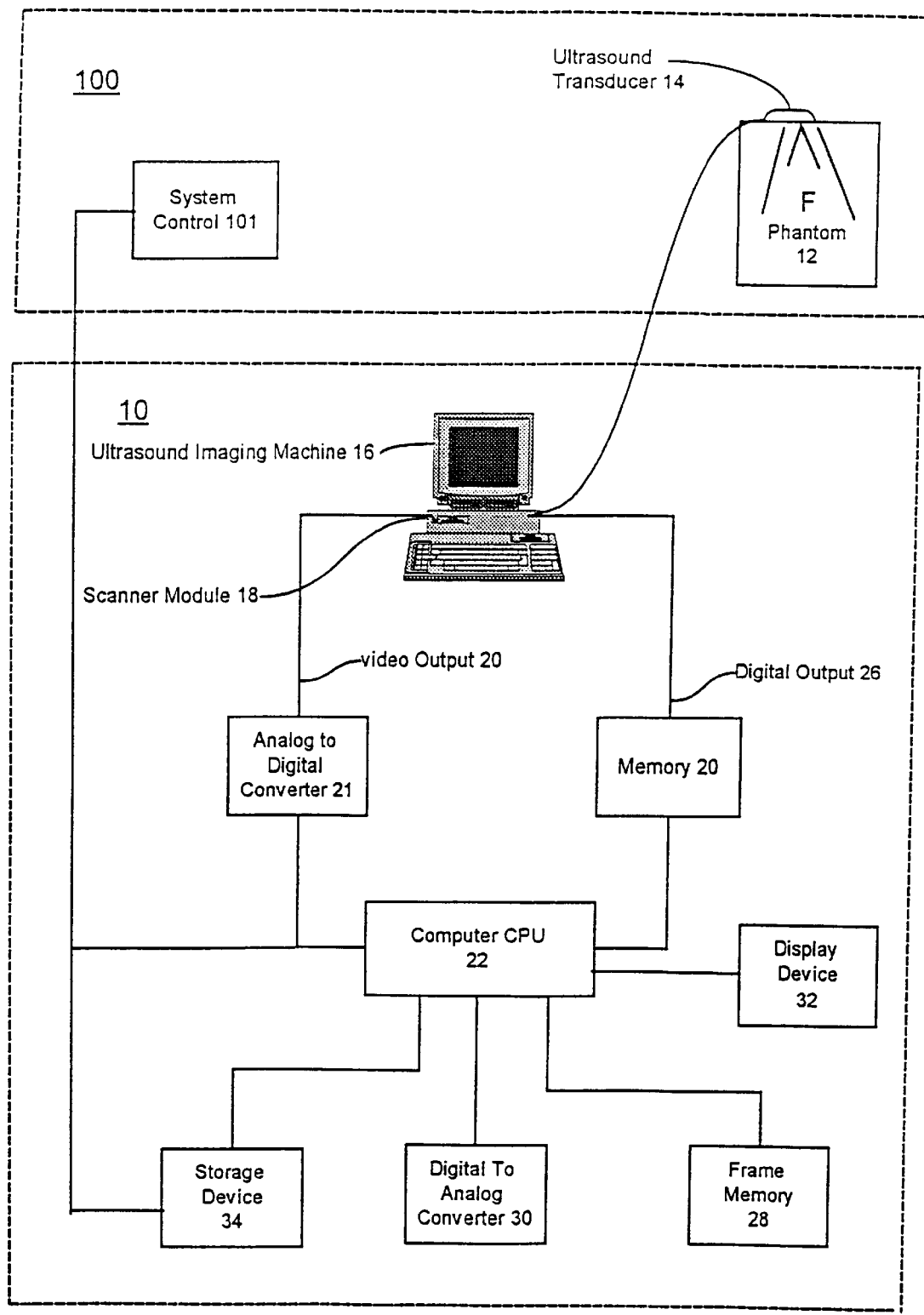
FIG. 2 is a block diagram of FIG. 1 illustrating the central element of the present invention in greater detail.

FIG. 2 is a block diagram of a control circuit for an ultrasound imaging system 10. The major components of system 10 include a standard phantom 12, an ultrasound probe 14, and an ultrasound imaging machine 16, all well known and commercially available. Ultrasound probe 14 is connected to, and is controlled by, a scanner module 18, which is connected to ultrasound imaging machine 16. Probe 14 emits an ultrasound irradiation field F that penetrates standard phantom 12 to be imaged. Ultrasound signals reflected from structures within phantom 12 are, in turn, received by probe 14 and processed to form acquired images in one of two known alternative modes by scanner module 18. In an analog mode, scanner module 18 outputs a video output 20 to an analog to digital converter, and the resulting image data is transferred to memory 22 of computer 24. Alternatively, in a digital mode of image acquisition, scanner module 18 outputs a digital output 26 to memory 20.

The reflected signals received by probe 14 are processed by computer 24 to form a reproduced ultrasound image of standard phantom 12, which is stored in frame memories 28. On a demand basis, the reproduced ultrasound image is converted into an analog signal by digital-to-analog (D/A) converter 30, and then displayed via an image display device 32, such as a CRT (cathode-ray tube) display. Connection to other well known output devices such as pen plotters, not shown, are envisioned. Operator control and input are accomplished via input device 34, such as a mouse or keyboard, connected to imaging machine 16.

A phantom is an assembly of a uniform background gel material that mimics human tissue in terms of ultrasonic attenuation and scattering absorption and dispersion. Examples of human tissue features mimicked in a phantom include liver tissues, tumors and cysts. In addition, there are included high reflectance objects, called "pins", which are arranged at precisely defined orientations and distances from each other, and are embedded in the uniform background gel material. A pin is a very small, (compared to the resolution of the imaging machine) high reflectance object, that mimics infinitely small point. Use of pin targets determines the accuracy of reproduction of vertical and horizontal dimensions and distances. For example, a set of evenly spaced vertical pins and a separate set of evenly spaced horizontal pins are used to measure the horizontal and vertical linearity of an image.

According to the invention, phantom 12 preferably is the Gammex RMI*405GS precision resolution grayscale test instrument, manufactured by Gammex, Inc., of Milwaukee, Wis. is a suitable standard phantom. (*Gammex RMI is a registered trademark of Gammex, Inc., Milwaukee, Wis.) As will be discussed in detail, a quantitative analysis of a reproduced image of the standard phantom by the image machine 10 under test, determines the extent to which the image machine 10 is operating according to the manufacturer's specifications.

Referring to the circuit shown in FIG. 2, the storage device 34 connected to computer 22, stores operating system programs and utilities required for operation of computer 22. According to the invention, storage device 34 also is arranged to store programmed system control 101, which is a computer program that controls the operation of system 10 and interfaces with the user. System control 101 includes processing steps for measuring image parameters and generating and comparing image quality indices of the reproduced ultrasound image of the standard phantom. The stored programmed steps compare the image quality indices generated from a reproduced test ultrasound image of the standard phantom with the stored pre-determined "gold standard" set of quality indices derived from the same phantom by a same-model in good operating order and provide the results for display and output.

Storage device 34 also is arranged to store a gold standard image representation of a standard phantom, a test ultrasound image representation of the same standard phantom, and associated measured parameters and calculated indices associated with each image. Optionally, more than one gold standard image representation, each representing a phantom of a different manufacture or different physical design, are stored. Likewise, optionally, for any given standard phantom, more than one set of gold standard image representations with associated parameters and indices, each set representing a unique model ultrasound image machine, are stored. Each gold standard set of indices, to be described in greater detail, corresponds to a reproduced image of a selected standard phantom obtained by a given model ultrasound imaging machine in good operating order under a selected operating conditions. The gold standard is intended to represent, as closely as possible, an optimum image representation, and for description purposes herein, is called an "optimum image representation".

Figure 3:
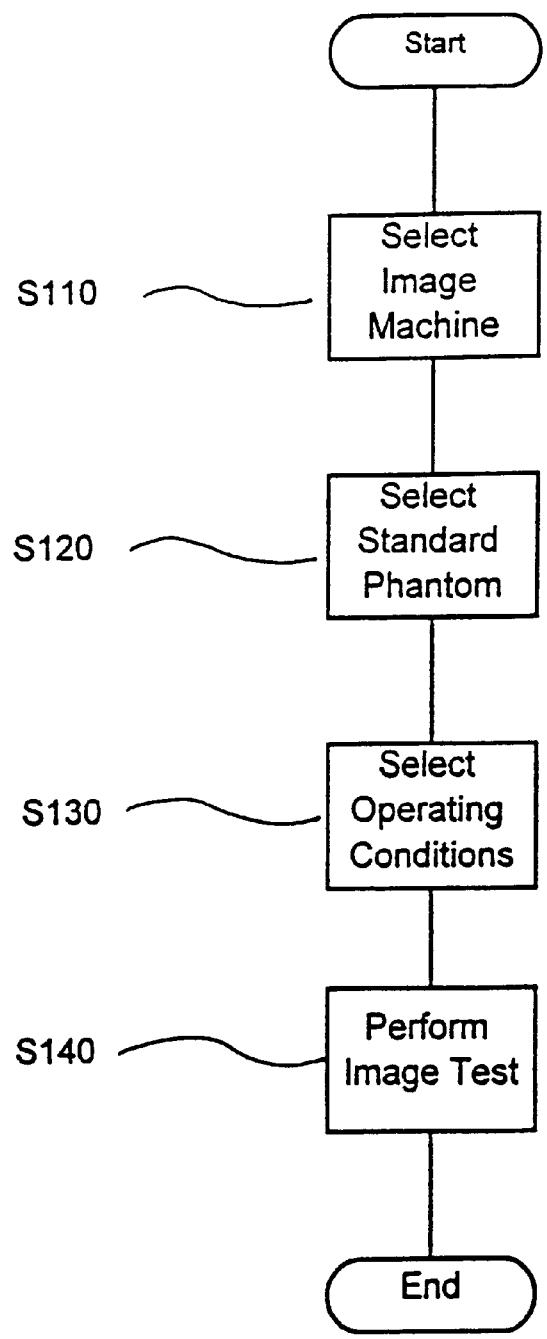
FIG. 3 is a simplified block diagram illustrating the steps for generating system control according to the present invention.

FIG. 3 is a simplified block diagram illustrating system control 101 of the present invention. While any suitable sequence of steps necessary to initialize the system will suffice, one sequence illustrated in FIG. 2 consists of a series of prompts directed to the user by system control 101. The first of such prompts is step S110, in which the user is prompted to select a specific model ultrasound image machine to be tested. At step S120, the user is prompted to select the specific standard phantom to be used during the test. As will be explained in detail, the selected model phantom must correspond to the phantom used during the current test of the ultrasound machine. At step S130, the user is prompted to select specific operating conditions under which the test will be performed. For example, various application settings such as gain and signal level, which are particular to the specific model machine under test and to the type of phantom used, is communicated to system control 101. Other factors, such as the type of probe are also entered. Each of these inputs corresponds to selections of specific parameters arranged in a look-up table or in an equivalent storage means, so that the remaining steps of the present invention are tailored to a particular machine, phantom, probe and settings. At step S140, system control 101 performs the test protocol, described next.

Figure 4:
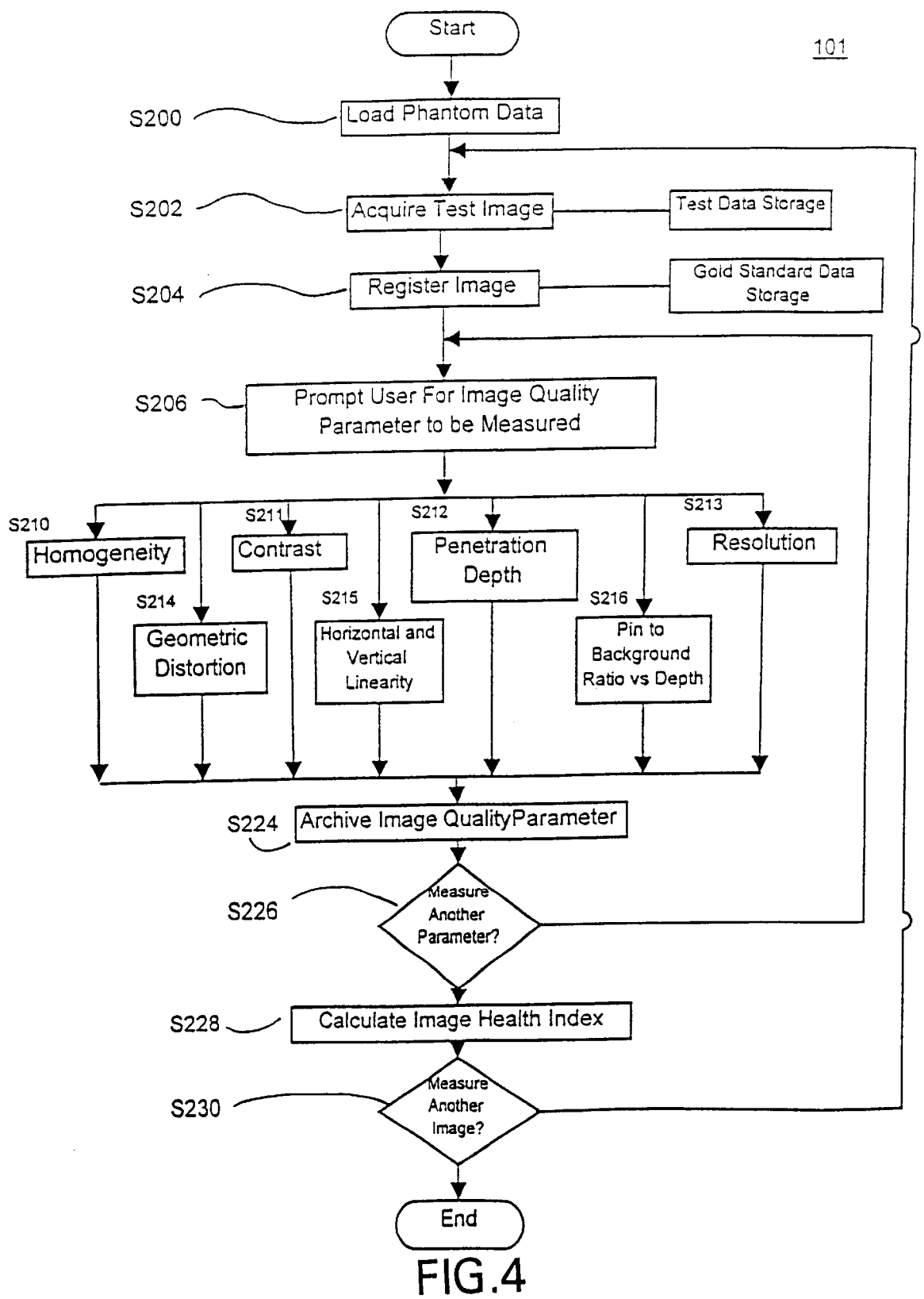
FIG. 4 is a simplified block diagram illustrating in greater detail the system control shown in FIG. 3.

FIG. 4 is a block diagram illustrating system control 101 in greater detail. At step S200, system control 101 prompts the user to load data corresponding to a standard phantom selected by the user. In one embodiment, the data is loaded into memory 22 from storage device 34. The loaded data includes a gold standard image representation of the selected standard phantom acquired by the same model machine as the machine to be tested by the user, along with gold standard quality indices and related parameters corresponding to the standard image. The gold standard data has been previously collected under ideal operating conditions by a machine tuned to recommended factory settings, and adjusted to the same conditions as input to system control 101 by the user at steps S120 and S130.

At step S202, the user is prompted to input data representing an ultrasound scan of the standard phantom acquired contemporaneously by the imaging machine under test. System control 101 stores the resulting test ultrasound image representation of the phantom in memory 20, as shown in FIG. 2. Alternatively, the image representation is stored in storage device 34 and made available to memory 22, as required.

Figure 5:
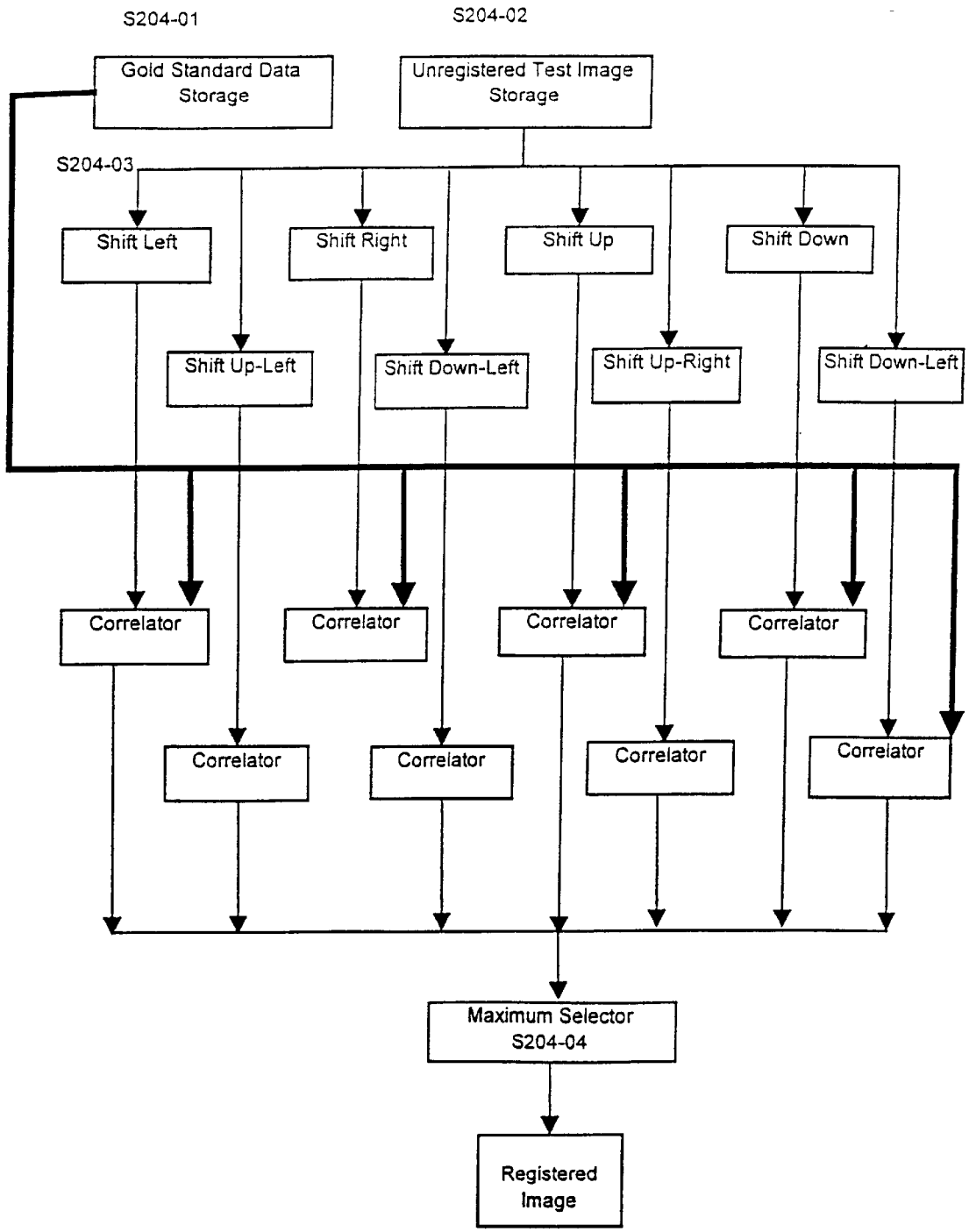
FIG. 5 is a simplified block diagram illustrating in greater detail the image registration step shown in FIG. 4.

FIG. 5 is a simplified block diagram illustrating the image registration step S204 in detail. At step S204, system control 101 performs an image registration function so that parameters associated with specific regions of the test image and parameters associated with corresponding regions of the standard phantom image are compared. Step S204 is an algorithm programmed to achieve registration without user intervention, in which system control 101 loads the test image from storage into memory 22.

At step S204-02, system control 101 obtains the gold standard phantom image representation and related parameter data from storage device 34. Because the test image is a representation of the same phantom used to obtain the gold standard image representation, it is possible to align, to a reasonable degree of precision, the test and phantom image representations, so that various parameters of the test image are measured and compared with those of the phantom image. However, as initially read from storage, the test image is "unregistered", which means that system control 101 is unable to "identify" spatially aligned features that are in common between the test image and the gold standard image. Thus, in step S204, system control 101 performs the task of shifting the test image representation until it is in alignment with the phantom image representation.

At step S204-03, system 101 compares the test and gold standard image representations by sequentially shifting the test image one pixel at a time in each of eight different directions. As shown in FIG. 5, these eight alternative directions include "shift left", "shift right", "shift up", "shift down", "shift up-left", "shift down-left", "shift up-right", and "shift down-right".

Also at step S204-03, system control 101 calculates a cross-correlation coefficient C for the entire image, for each of the above-mentioned single-pixel shifts. The cross-correlation coefficient represents a quantitative degree of preference toward, or away from, registration of the test and gold standard image representations. If the "gold standard" phantom image is defined by pixels $I_1(i,j)$ and the test image T is defined by pixels $I_2(i,j)$, the cross-correlation coefficient C is defined as:

$$C = \frac{\sum_{i,j} I_1(i,j) I_2(i,j)}{\sqrt{\sum_{i,j} I_1^2(i,j) \sum_{i,j} I_2^2(i,j)}}$$

Including the original position, these one-pixel shifts generate nine versions of the image. Each one-pixel shift is followed by calculation and storage of the cross-correlation coefficient C, which represents the degree to which the entire image has been shifted toward, or away from, precise registration.

At step S204-04, the acquired cross-correlation coefficients C are compared and the incremental directions having the maximum correlation are sequentially selected, until the unregistered test image representation is shifted, as necessary, to the right, left, up down, up-left, down-left, up-right, and down-right. This process continues until the test image is in registration with the gold standard representation of the phantom image, to a pre-determined acceptable degree of accuracy.

The correlation coefficient C also serves as a gross image similarity metric, i.e., when coefficient C is below a pre-defined threshold, such as 50% or 60%, the test image quality is deemed to be too low or a wrong reference has been used. Typically, correlations of 80%, or more, are desirable.

Returning to FIG. 4, after image registration is achieved, system control 101 commences at step S206 with a cycle of prompting the user for selection of a series of image quality indices to be calculated, until all selections have been made. After all selections have been entered, system control 101 calculates and displays the Image Health Index. During each cycle, at steps S210–S216, pertinent parameters (described in detail, below) are calculated and stored for associated image quality indices, including Homogeneity, Contrast, Signal Attenuation, Pin to Background Ratio, Resolution, Geometric Distortion, and Axial and Lateral Linearity. For generation of each of these indices, the user is prompted to select a region of interest of the test image that includes features suitable for measuring image quality parameters that system control 101 uses to generate the respective image quality index. For example, the typical test image of the standard phantom includes areas of uniformity, as well as a variety of imaged objects or "targets". Each area or target is designed to be appropriate for determining the parameters of one or more image quality indices.

At step S224, the parameters associated with each index are stored after calculation of the associated image quality index selection. At step S226, system control 101 prompts the user with the option of measuring another image quality parameter. Alternatively, system control 101 computes and displays the Image health index at step S228. At step S230, the option of evaluating another test image is presented, causing system control 101 to direct control back to step S202, where the system prompts the user to load a test image. Alternatively, system control 101 directs the user to end the procedure.

Figure 6:
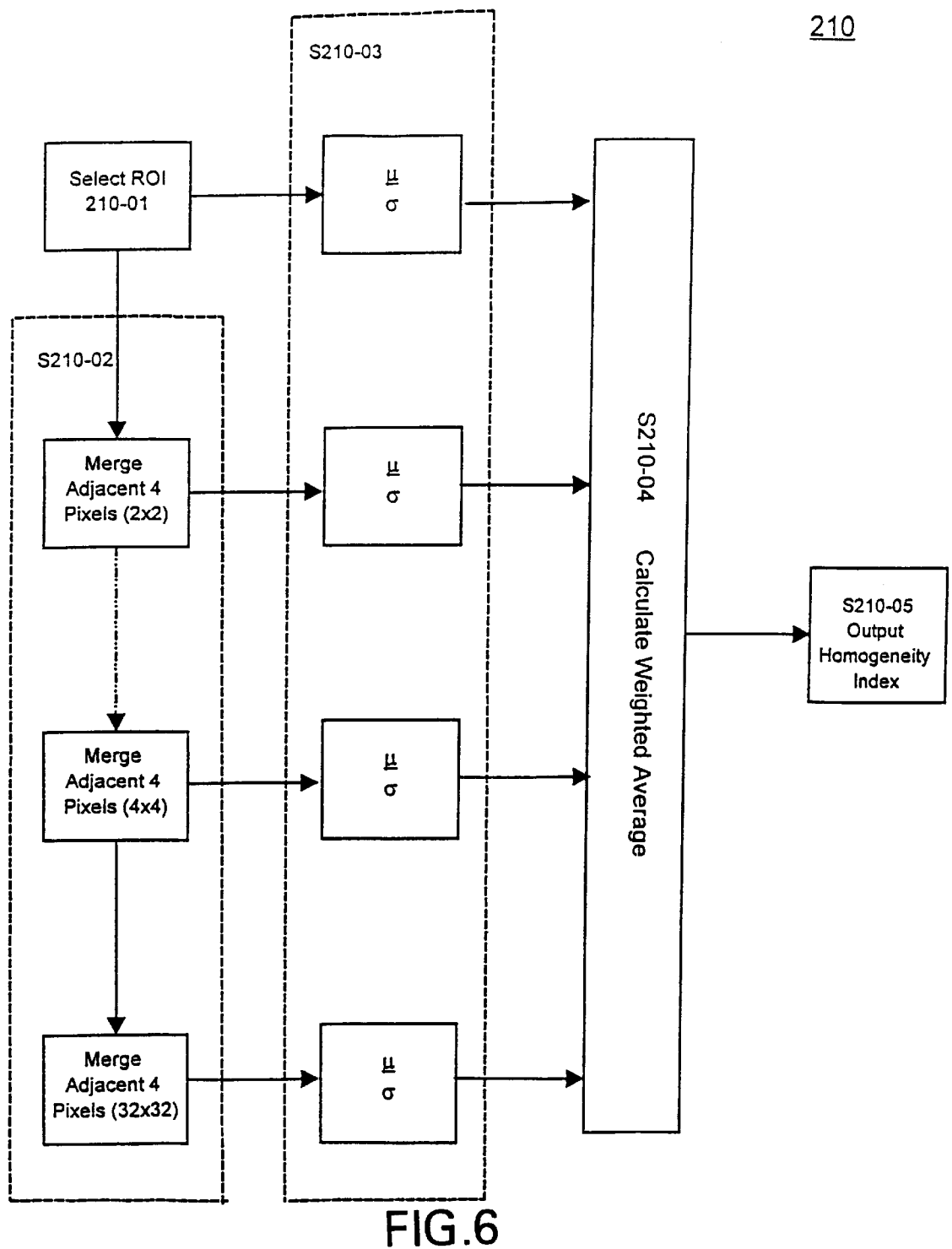
FIG. 6 is a simplified block diagram illustrating steps for generating the Homogeneity image quality index according to the present invention.

FIG. 6 is a simplified block diagram illustrating the steps for generating the Homogeneity image quality index. This is the first of the above-mentioned seven image quality indices. For this index, the user selects a region of the image that contains a uniform background area with no target present. This is accomplished in step S210-01, in which system control 101 prompts the user to select a region of interest from a display of the test ultrasound image. This is best accomplished through the use of a commonly known graphical user interface and graphical input techniques. Advantageously, according to the invention, a choice of several square-shaped selection-fields of differing pixel sizes is provided on the display screen, along with a facility for the user to associate one of these selection-fields with a region of interest on the test image. The user makes a selection among the visible options on the display screen, for example, with a mouse or keyboard entry. This input communicates the chosen region of interest to system control 101.

At step S210-02, system control 101 calculates a multi-resolution scale for the selected region of interest. With such a scale, at low resolution, the image is expected to be more homogeneous than at high resolution. The scale is calculated by first dividing the region of interest into N 32 pixel×32 pixel blocks and then computing the average pixel brightness, i.e., the mean $\mu$, of each block, where N is an integer. Next, the standard deviation $\sigma$ of the brightness of each block is calculated. The homogeneity at this resolution is the standard deviation of the brightness of the N blocks, normalized by the mean $\mu$ of the brightness of the N blocks, i.e., for M pixels in a block, the ratio of the mean $\mu$ to the standard deviation $\sigma$ is calculated as follows:

$$\mu = \frac{1}{N}\sum_{i,j} P(i,j) \quad \sigma = \sqrt{\frac{1}{N}\sum_{i,j} P^2(i,j) - \mu^2}$$

Next, the system divides each of the N blocks into four blocks. At this point, the region of interest includes 4N blocks of size 16×16. The homogeneity at this resolution is the standard deviation of the brightness of the 4N blocks, normalized by their mean. This calculation is repeated for 16N blocks of size 4×4, etc., until a single pixel size block is reached.

A step S210-03, all homogeneity ratios are calculated, and at step S210-04, a weighted the average of all homogeneity ratios is calculated. The result is outputted at step S210-05, called the Homogeneity image quality index and made available for subsequent use by system controller 101.

Figure 7:
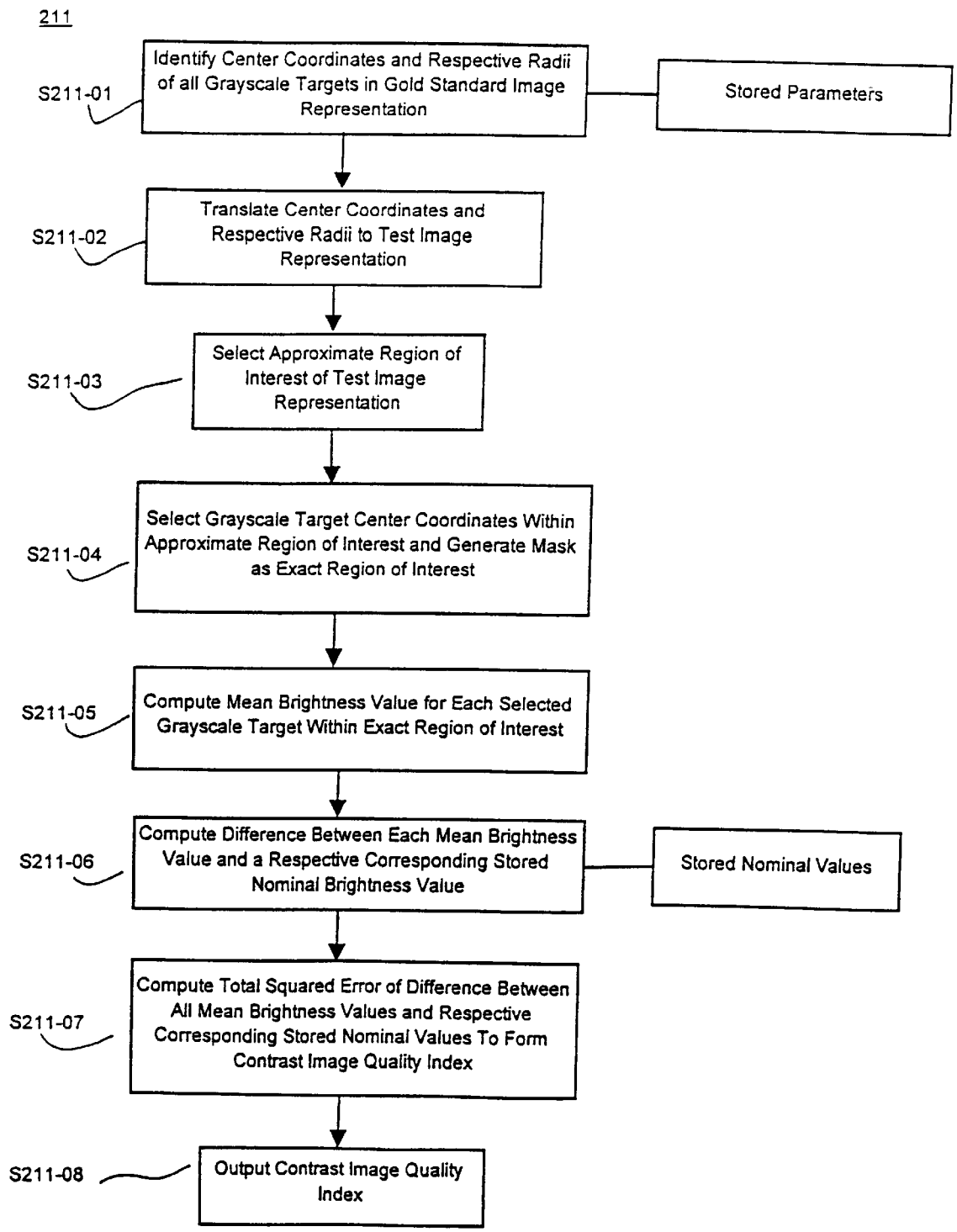
FIG. 7 is a simplified block diagram illustrating steps for generating the Contrast image quality index according to the present invention.

FIG. 7 is a simplified block diagram illustrating the steps for generating the Contrast image quality index, which is the second of the seven image quality indices available for selection at step S206 of FIG. 4. The Contrast image quality index is determined by measuring and comparing the brightness level of targets having a uniform grayscale level. Anechoic cystic objects are an example of such targets. To accomplish this, at step S211-01, system control 101 retrieves stored data as necessary and identifies the center coordinates and respective radii of all grayscale targets in the optimum image representation.

At step S211-02, system control 101 translates the center coordinates and respective radii to the test ultrasound image representation.

At step S211-03, system control 101 prompts the user to select an approximate region of interest of the test image. The appropriate region is one that contains a target group of four uniformly grayscale targets, according to the present invention.

At step S211-04, system control 101 System control 101 selects at least one grayscale target center coordinate within the approximate region of interest and generates a mask based on all selected grayscale target center coordinates and respective radii. The collection of pixels under the mask is an exact region of interest. It will be recalled that the stored data includes actual spatial and dimensional measurements of targets representing the same standard phantom that is used to generate the test ultrasound image representation. Therefore, the stored coordinates and related measurements apply to corresponding targets represented in the test ultrasound image representation.

At step S211-05, system control 101 computes a mean brightness value for each selected grayscale target within the exact region of interest. At step S211-06, system control 101 converts the result to the decibel scale (dB), which is a base ten log scale, by methods commonly known in the art, and then computes the difference between each mean brightness value and a respective corresponding nominal brightness value obtained from the optimum image representation. For example, using a commonly available standard phantom and a typical model image machine, the decibel scale values obtained for four grayscale objects in the test image made with that machine, are compared with nominal values −18, 16, +6 and +18, which were obtained by the same model image machine in good working order and under good operating conditions.

At step S211-07, system control 101 computes the contrast image quality index by computing a total squared error of the difference between all mean brightness values and respective corresponding nominal values, and at step S211-08, the Contrast image quality index is outputted and made available for subsequent use by system control 101.

Figure 8:
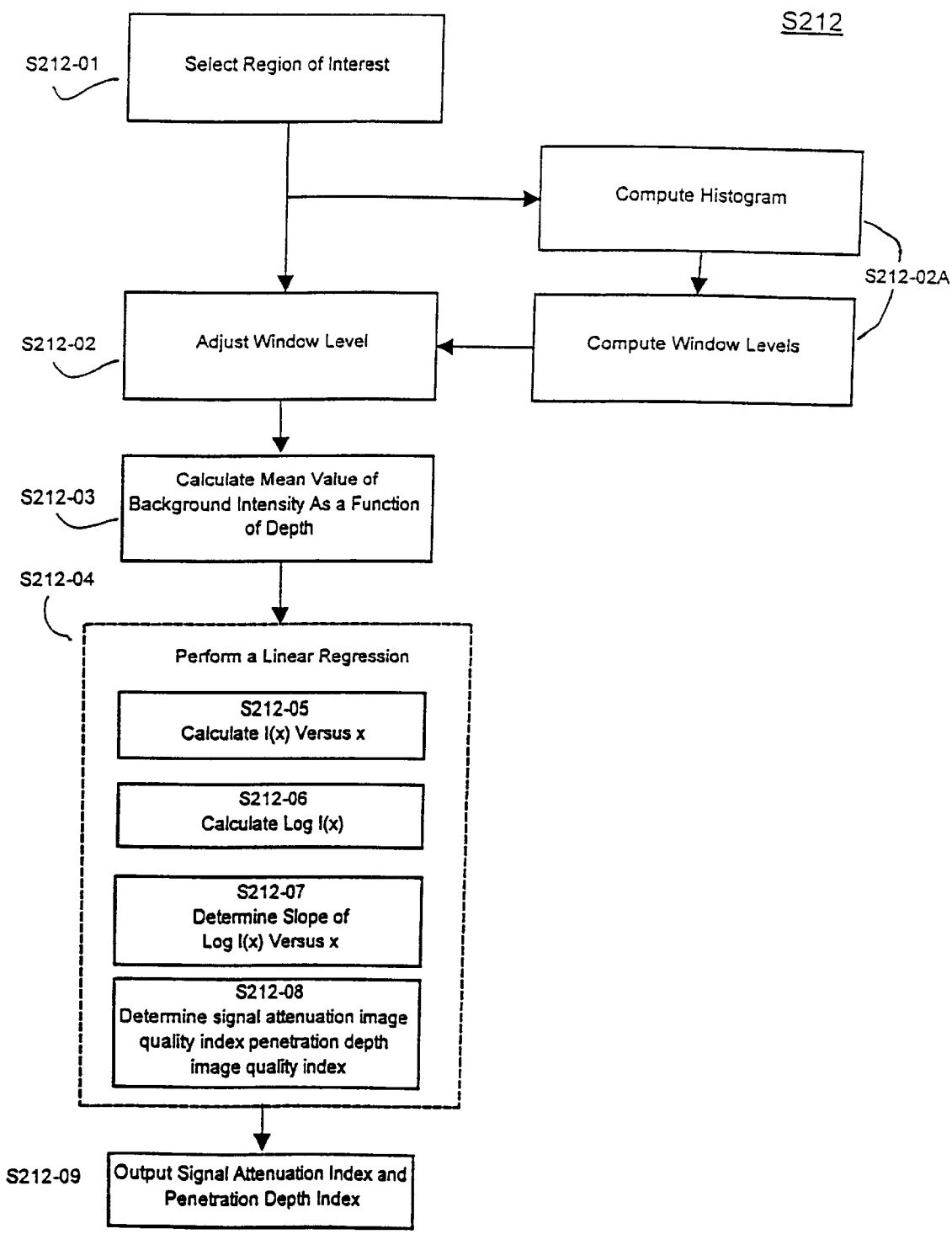
FIG. 8 is a simplified block diagram illustrating steps for generating the Signal Attenuation index and Penetration Depth image quality index according to the present invention.

FIG. 8 is a simplified block diagram illustrating the steps for generating the Signal Attenuation and Penetration Depth image quality index, which is the third of the seven image quality indices available for selection at step S206 of FIG. 4. At step S212-01, system control 101 prompts the user to select an approximate region of interest of the test ultrasound image representation. According to the invention, the appropriate region contains a uniform background area with no target present. Generally, during the formation of a test image, the energy of an ultrasonic echo from the tissue-like gel of the standard phantom decreases as depth of the gel increases, just as it would in actual, target-free, human tissue. In a normally functioning machine, this decrease in reflected energy is compensated by auto gain control circuitry. However, a malfunction of the probe could result in abnormal signal attenuation and loss of depth of signal penetration. When this happens, the resulting fade of reflected energy is difficult to distinguish from a true depth-dependent reflected energy level. Therefore, to determine the Signal Attenuation and Penetration Depth image quality index, the selected region must contain a large background volume with no interfering target present.

At step S212-02, the system control 101 prompts the user to identify the grayscale levels of interest, known as "window leveling". At the option of the user, at step S212-02A, the system control 101 computes, and displays for the user to see, a histogram-type spectrum of gray levels populating the approximate region of interest. This spectrum quantifies the various gray levels present, and permits the user to discard spurious gray levels that are far from the majority, and which would incorrectly skew an average signal intensity measurement.

The signal attenuation image quality parameter is modeled as intensity profile $I(x)=I_0 e^{-\lambda x}$, where $I(x)$ is the background mean intensity at depth x, and $\lambda$ is the attenuation parameter. The attenuation parameter $\lambda$ is calculated by a linear regression method signified by step S212-03, which includes calculations performed according to known methods indicated at steps S212-04 through S212-06. In step S212-04, the mean of the background, i.e., the pixel brightness, of various depths is calculated to obtain the intensity profile I(x), which is brightness as a function of depth. At step S212-05, log I(x) is calculated, and then at step S212-06, a straight line is drawn through log I(x) versus x. The negative of the slope is an estimate of λ, and is the signal attenuation index. Equivalently, 1/λ is the penetration depth index. At step S212-07, the signal attenuation index and the penetration depth index are outputted, and made available for subsequent use by system control 101.

Figure 9:
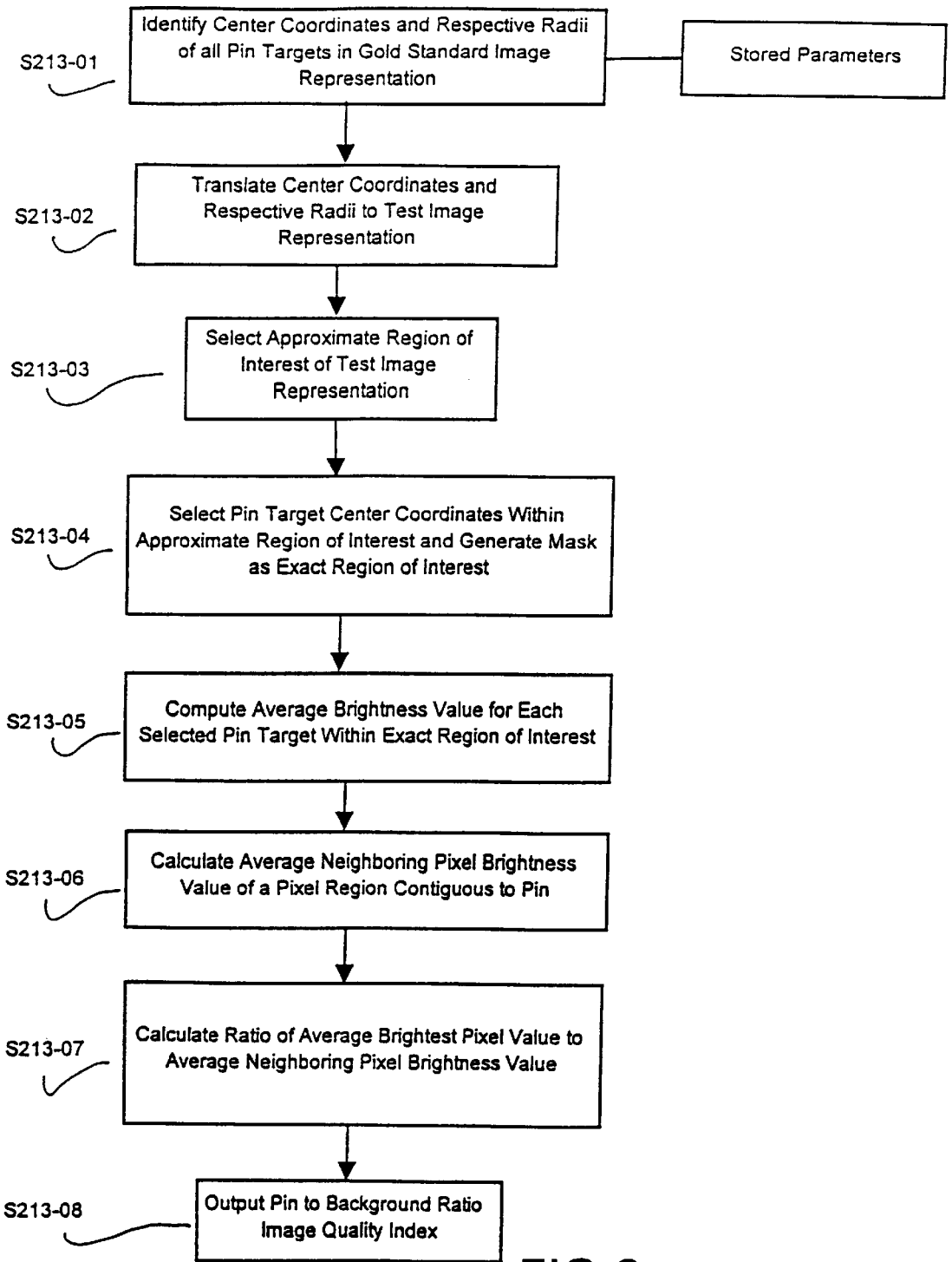
FIG. 9 is a simplified block diagram illustrating steps for generating the Pin to Background Ratio image quality index according to the present invention.

FIG. 9 is a simplified block diagram illustrating the steps for generating the Pin to Background Ratio (PBR) image quality index, which is the fourth of the seven image quality indices available for selection at step S206 of FIG. 4. The Pin to Background Ratio, also known as signal-to-noise ratio, is computed at each depth as the ratio of the mean of energy from a strongly scattering pin to the mean of the background region surrounding the pin. At step S213-01, system control 101 prompts the user to select a region of interest of the test image. The region appropriate for the PBR image quality index includes evenly spaced, vertical pins imbedded at specific depths in an otherwise target-free background gel.

At step S213-02, system control 101 calculates the locations of the pins by a method known as "local maxima detection". This method includes selection of a specified size neighborhood, e.g., 10×10 pixels, of the stored pin locations, which establishes a baseline grayscale brightness. Next, system control 101 selects the brightest pixel in the selected neighborhood. The location of this pixel is the location of the pin in the test image, and the difference between the pin's pixel brightness and that of the baseline brightness, i.e., the total squared error is the Pin to Background Ratio. Ideally, the pin should be just a single bright pixel, but in the test image, it will be a group of contiguous pixels with brightness decreasing from the maximum to that of the background. The function of this decrease in brightness describes the profile curve of the pin, with the ideal, single-pixel pin being a single spike.

Thus, for an actual pin at a selected depth, at step S213-03, the energy reflected from the pin is measured as an average of the pixel intensity for the area of the pin. At the same time, at step S213-04, the average pixel intensity of a region neighboring the pin is measured. At step S213-05, the ratio of the mean of the pixel intensity representing the energy reflected from the strongly scattering pin to the mean of the pixel intensity representing the energy reflected from the background neighboring the pin is calculated as the Pin to Background Ratio image quality index. This index is calculated for pins at various selected depth locations represented in the test image. At step S213-06, the Pin to Background Ratio image quality index is outputted and made available for subsequent use by system control 101.

Figure 10:
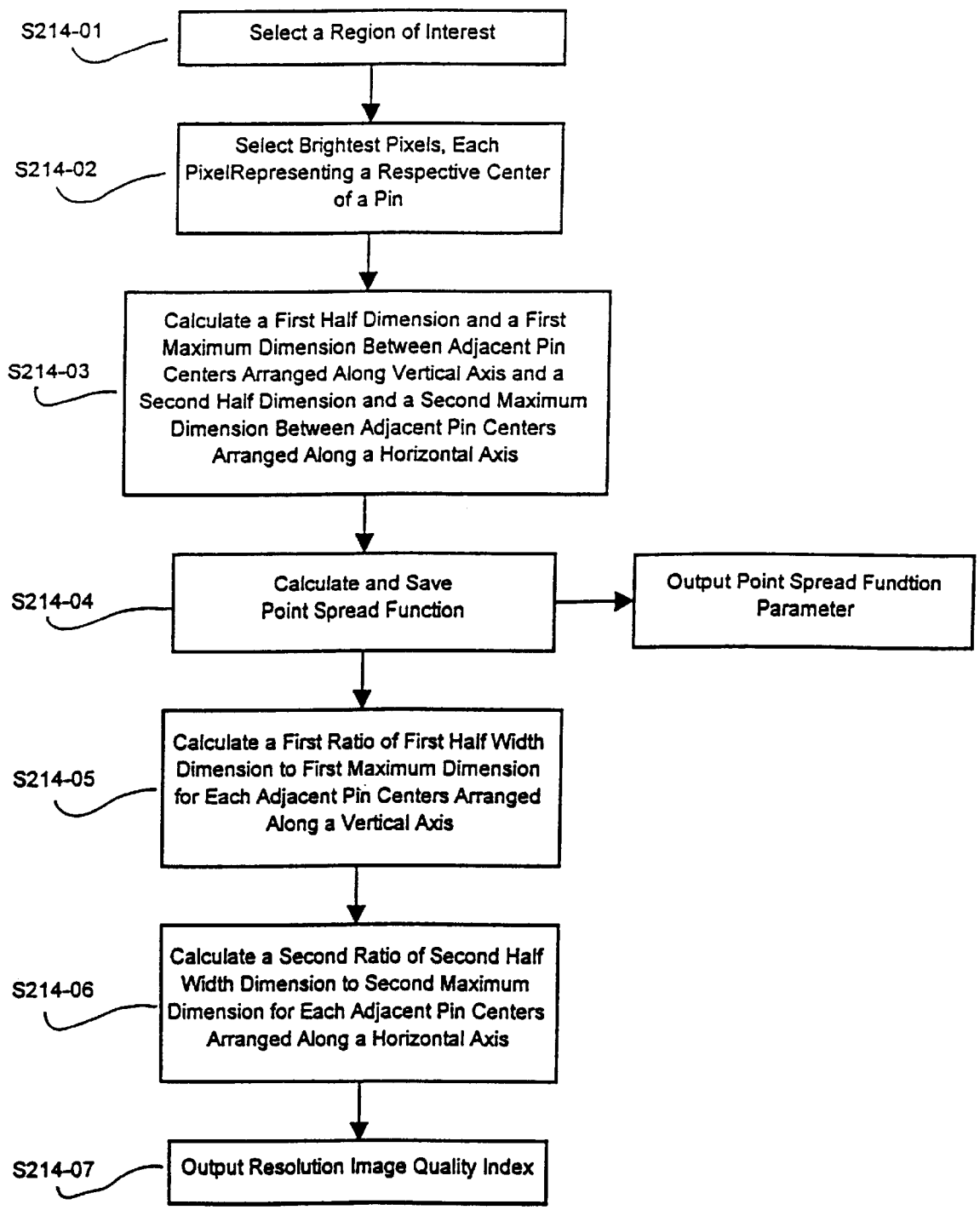
FIG. 10 is a simplified block diagram illustrating steps for generating the Resolution image quality index according to the present invention.

FIG. 10 is a simplified block diagram illustrating the steps for generating the Resolution image quality index, which is the fifth of the seven image quality indices available for selection at step S206 of FIG. 4. The Resolution index is determined by comparing how the pixel brightness of pin targets varies with the brightness of their neighboring background. In general, resolution is described in terms of axial and lateral resolution. By measuring which pairs of pins are resolvable at various depths, the axial and lateral resolution parameters are estimated in terms of millimeters. The Resolution index includes the calculation of a point spread function, which is simply the measurement of the resolution of an isolated pin.

At step S214-01, system control 101 prompts the user to select a region of interest of the test ultrasound image representation that includes evenly spaced, vertical pins imbedded at specific depths in a background gel.

At step S214-02, system control 101 first detects local maxima by the same method described in connection with step S213-02, which identifies areas of strong and weak pixel brightness, and selects the brightest pixel value in the selected neighborhood. System control 101 does this by selecting a brightest pixel value in the selected region of interest by measuring a second average pixel intensity of a pixel region neighboring the pin, said brightest pixel value representing a pin. System control 101 then selects a pixel brightness value of a pixel region neighboring said selected brightest pixel value, after which, system control 101 calculates a ratio of the first and second average pixel intensities, wherein the ratio is the pin to background ratio image quality index. The coordinates of the brightest pixel represent the location of the pin in the test image. In this way, system control 101 determines the locations of adjacent pairs of pin arranged along a vertical axis and pairs arranged along a horizontal axis.

At step S214-03, through a known process of interpolation, system control 101 calculates distances between adjacent pin profiles. The distances are calculated by selecting a region of the test ultrasound image representation that includes at least two evenly spaced pins arranged along a vertical axis and at least two evenly spaced pins arranged along a horizontal axis. Next, system control 101 selects the brightest pixels in the region of interest, each pixel representing a respective center of a pin.

At step S214-04, the measured profile of the test image is saved as a point spread function, to be made available for output to the user.

At step S214-05, system control 101 calculates a first half dimension and a first maximum dimension between adjacent pin centers arranged along a vertical axis, and a second half dimension and a second maximum dimension between adjacent pin centers arranged along a horizontal axis. System control 101 calculates a first ratio of the first half width dimension to the first maximum dimension for each adjacent pin centers arranged along a vertical axis, and calculates a second ratio of the second half width dimension to the second maximum dimension for each adjacent pin centers arranged along a horizontal axis. The first ratio is a vertical component of the Resolution Image Quality Index and the second ratio is a horizontal component of the Resolution Image Quality Index. At step S214-06, this index is outputted and made available for subsequent use by system control 101.

Figure 11:
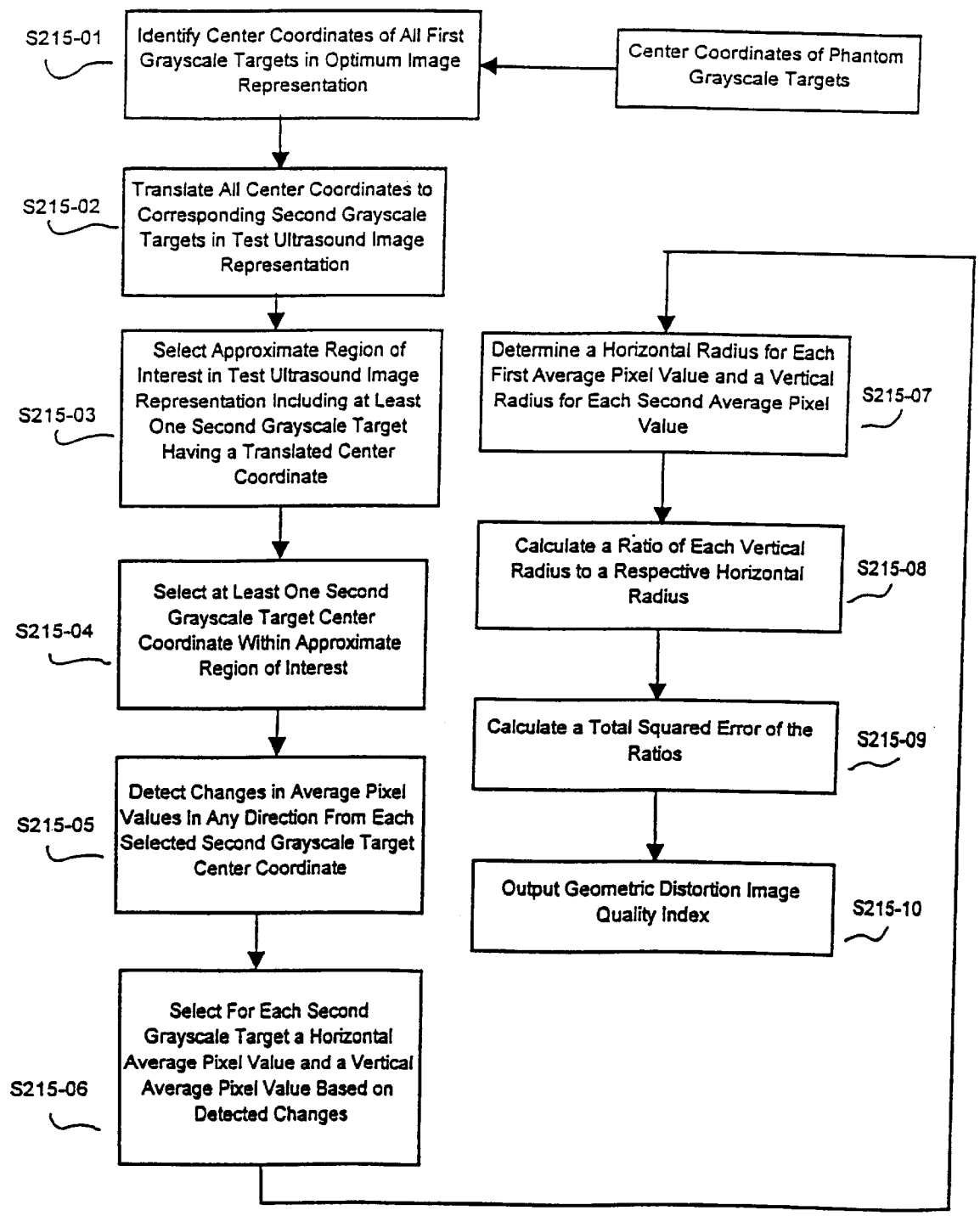
FIG. 11 is a simplified block diagram illustrating steps for generating the Geometric Distortion image quality index according to the present invention.

FIG. 11 is a simplified block diagram illustrating the steps for generating the Geometric Distortion image quality index, which is the sixth of the seven image quality indices available for selection at step S206 of FIG. 4.

At step S215-01, system control 101 prompts the user to select an approximate region of interest of the test image. According to the invention, the selected region contains an area including a grouping of grayscale objects representing anechoic cysts in human tissue and appears as having uniform grayscale shading. Preferably, although not required, this is the same target group used to determine the Contrast image quality index. Initially, the approximate region of interest selection procedure is the same as described above, in connection with step S210-01 in the procedure illustrated in FIG. 6. However, as in the determination of the Contrast index, a comparison of dimensional data between the test image representation of the phantom and the actual phantom itself is necessary. But, unlike the use of stored radii measurements to mask out the cysts in the determination of the Contrast index, here, the determination of the actual boundary of the cyst represented in the test image is required.

To determine the actual boundary of each cyst, at step S215-02, system control 101 recalls from storage predetermined measurements of center coordinates of the cysts in the actual phantom, and then system control 101 translates those measurements into test image coordinates. Those centers that fall within the approximate region of interest on the test image represent precisely definable coordinates that are in common between the test image and the actual phantom.

At step S215-03, using these precise coordinates of the centers of the grayscale target cysts, the edges of each test image grayscale target are located by well known adaptive edge detection techniques. This technique detects abrupt changes in average pixel values in any direction, to attempt to identify an edge of the image.

Next, at step S215-04, the principal axis lengths, i.e., the horizontal and vertical radii of each grayscale target are measured, and at step S215-05, the average ratio of the horizontal and vertical radii is calculated for each grayscale target. For a distortionless image, this average ratio should be the same as a corresponding predetermined ratio of the actual phantom. The degree that it is not the same, i.e., the total squared error, indicates the amount of distortion. Preferably, another indication of distortion is obtained from the ratio of the radii of, for example, three cysts at the same depth. Because these ratios are precisely known for a given standard phantom, for example, 6:4:2, such a ratio defines a distortionless image. The total squared error of this ratio, with respect to the test image and the actual phantom, is the Geometric Distortion image quality index calculated in step S215-06. At step S215-07, the Geometric Distortion index is outputted and made available for subsequent use by system control 101.

Figure 12:
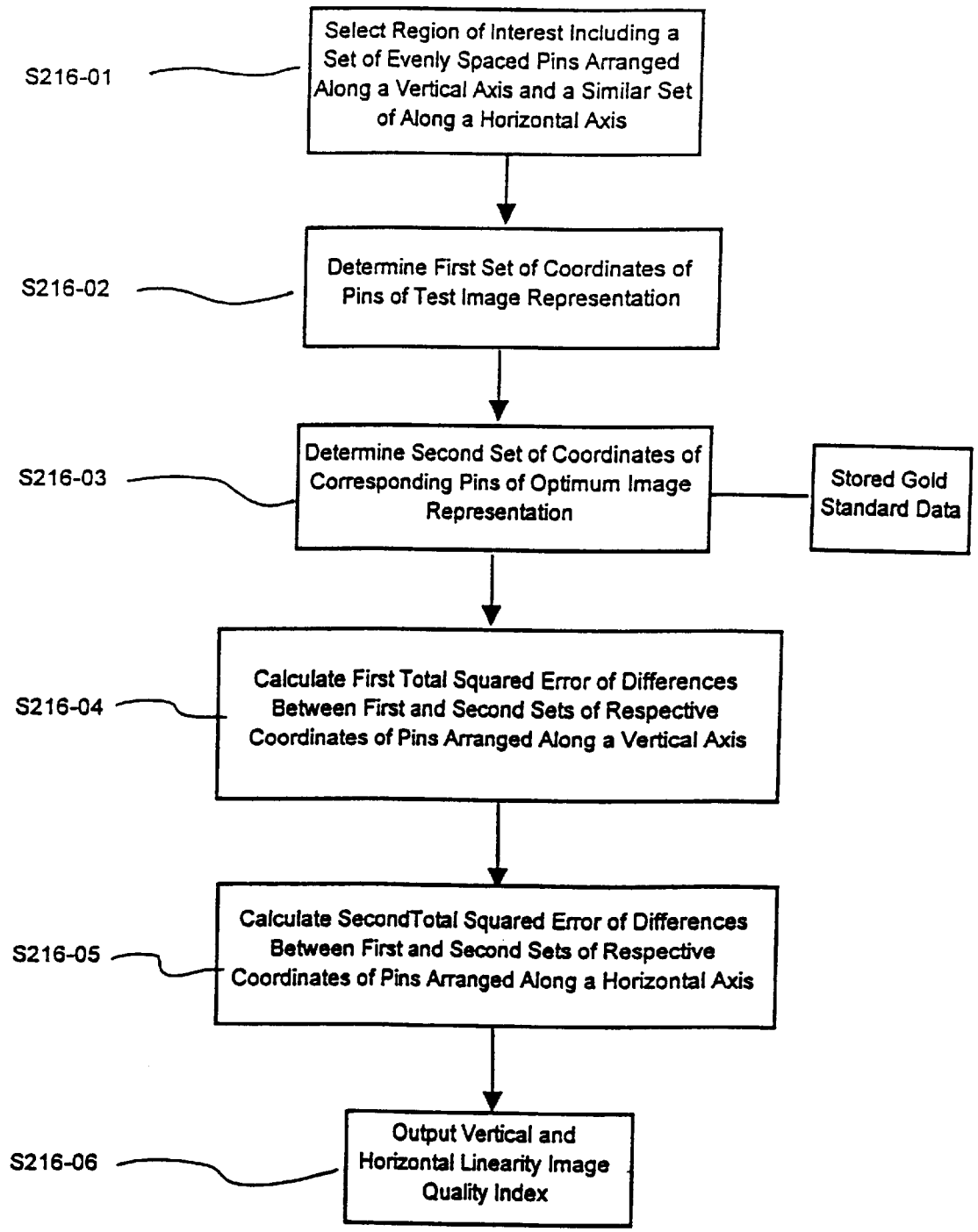
FIG. 12 is a simplified block diagram illustrating steps for generating the Vertical and Horizontal Linearity image quality index according to the present invention.

FIG. 12 is a simplified block diagram illustrating the steps for generating the Linearity image quality index, the seventh of the seven image quality indices. At step S216-01, system control 101 prompts the user to select a region of interest of the test image that includes evenly spaced pins arranged along a vertical axis and imbedded at specific depths in an otherwise target-free background gel. Using the method discussed above in connection with step S213-02, system control 101, at step S216-02, calculates the locations of the pins by the "local maxima detection" method. It will be recalled that this method determines the brightest pixel in the selected neighborhood, which corresponds to a pin, due to high reflectivity of pins in general. The location of this pixel is the location of the pin in the test image but possibly not the center of the pin. At step S216-03, the difference between the brightness level of neighboring background pixels and each pixel contiguous to the bright pixel, i.e., the total squared error, is calculated to determine the brightness profile of the pin, and from that profile, the center of the pin is determined. This calculation is made for each of the pins arranged along a vertical axis.

At step S216-04, the sum of the squared error of the pin coordinates between the test image and the coordinates of a corresponding pin in the actual phantom is calculated. The result is the Vertical Linearity image quality index. The same calculation is made for successive pairs of horizontally oriented pins, which produces the Horizontal Linearity image quality index. At step S216-05, these indices are outputted and made available for subsequent use by system control 101.

Figure 13:
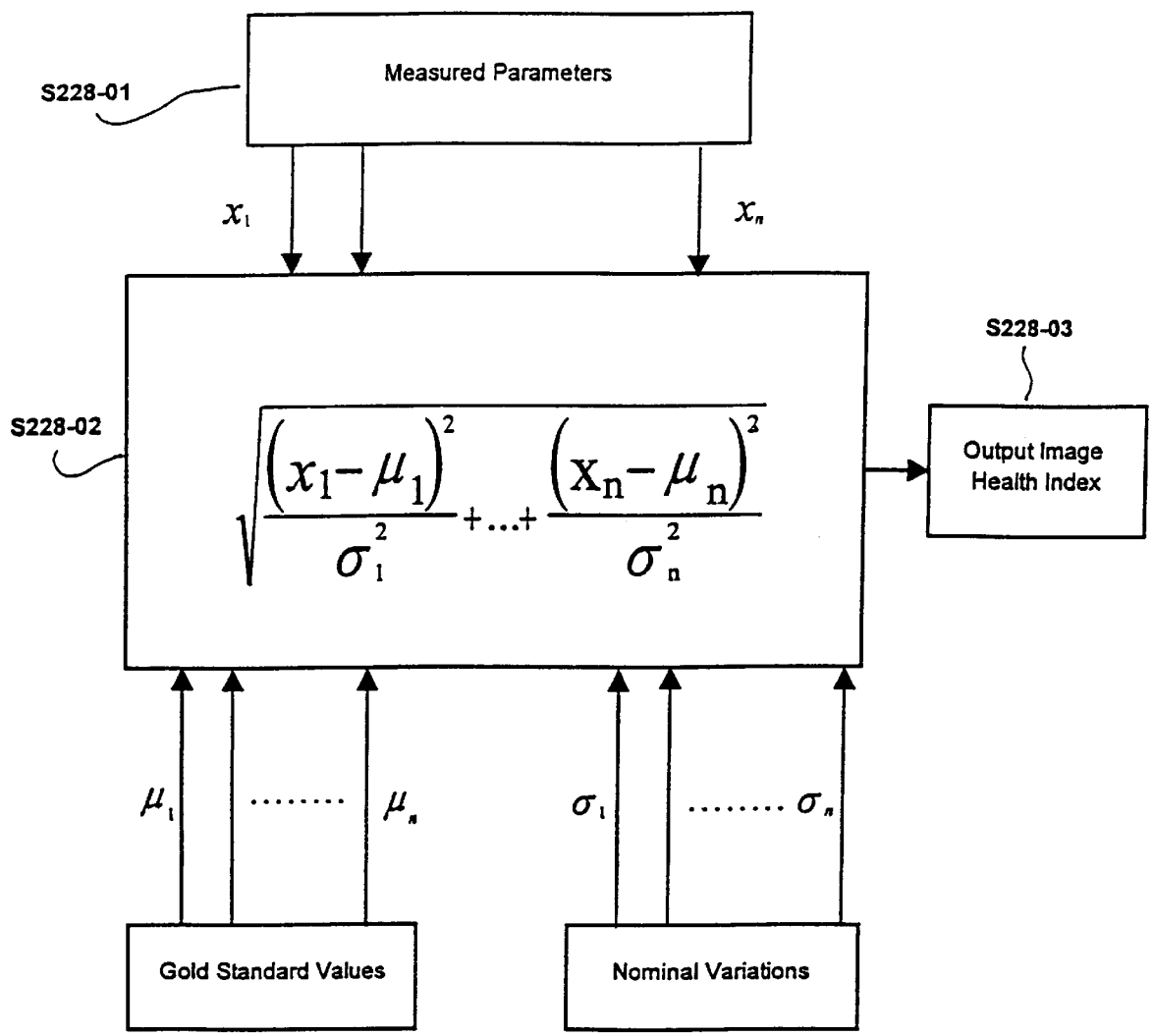
FIG. 13 is a simplified block diagram illustrating steps for generating the Image Health Index according to the present invention.

FIG. 13 is a simplified block diagram illustrating the steps for generating the Image Health Index. At step S228-01, all of the image quality indices $X_1 \ldots X_n$ are identified, and at step S228-02, the image quality indices are combined to form a single Image Health Index to indicate the overall accuracy of the test image. The Image Health Index takes into account statistical variations among normal, "healthy" images, and weighs each image quality parameter accordingly. The image variations are ideally determined from statistics of a significant number of gold standard images. For this purpose, the Manahalobis distance is represented by the square root of the sum of the squared difference between the image quality indices and the gold standard indices, divided by the square of the standard deviation of the parameters for all image quality indices. At step S228-02, system control 101 performs this calculation, which takes the following form $$\sqrt{\frac{(x_1 - \mu_1)^2}{\sigma_1^2} + \ldots + \frac{(x_n - \mu_n)^2}{\sigma_n^2}}$$

where $x_1 \ldots x_n$ are measured parameters, $\mu_1 \ldots \mu_n$ are gold standard values, and $\sigma_1 \ldots \sigma_n$ are nominal variations, for example, computed as the standard deviation of the measured parameters.

At step S228-03, the Image Health Index is output by any display device 32.

Optionally, other image quality indices are envisioned as included in the calculation of the Image Health Index. Alternatively, any number of image quality indices are used, as desired, to calculate the Image Health Index. For example, two indices such as the Resolution and the Linearity image quality indices, result in the corresponding values are shown in Table A.

TABLE A

|  | Measured Value | Gold Standard Value | Nominal Variation |
| --- | --- | --- | --- |
| Resolution | 2.4 mm | 2 mm | 0.5 mm |
| Linearity | 3 dB | 1 dB | 1 dB |

The Image Health Index is computed to be 2.15, which is a unitless number, when the values shown in Table A are applied to the equation shown step S228-02 of FIG. 13. Substitution of other values into the equation of FIG. 13 indicate that the Image Health Index, and the corresponding "health" of the test image becomes "better" as the ratio becomes progressively smaller, and the index becomes "best" when its value is zero. When the ratio is large, then the "health" of the test image is poor. It also is seen that as the nominal variations, $\sigma_n$, become large, then the difference becomes less significant.

What is claimed is:

1. A method of quantitatively evaluating image quality characteristics of an ultrasound imaging machine comprising the steps of:

storing an optimum ultrasound image representation of a phantom;

storing a test ultrasound image representation of said phantom, said test ultrasound image representation being obtained from an ultrasound instrument under test;

electronically and automatically shifting in memory the stored test ultrasound image representation until said representation is in registration with said optimum ultrasound image representation comparing one or more image quality parameters of the test ultrasound image with one or more regions of interest of the optimum stored ultrasound image representation with one or more corresponding regions of the test ultrasound image representation, each said one or more regions of interest corresponding to an image quality parameter to be evaluated;

calculating from the comparison a respective image quality index for each of said one or more regions of interest; and utilizing said image quality indices to calculate an image health index from said respective image quality indices, wherein said image health index quantitatively represents image quality characteristics of the ultrasound imaging machine under test.

2. The method of claim 1, wherein said shifting the test ultrasound image representation includes calculation of a cross-correlation coefficient, said cross-correlation coefficient representing a quantitative degree of proximity of coordinates of features in said test image representation relative to coordinates of corresponding features in said optimum image representation.

3. The method of claim 2, wherein said cross-correlation index is given by $$C = \frac{\sum_{i,j} I_1(i,j) I_2(i,j)}{\sqrt{\sum_{i,j} I_1^2(i,j) \sum_{i,j} I_2^2(i,j)}}$$

wherein C equals the cross-correlation coefficient, $I_1(i,j)$ equals test image pixel locations, and $I_2(i,j)$ equals optimum image pixel locations.

4. The method of claim 1, wherein said image quality index is a homogeneity image quality index calculated by:

selecting a region of the image of said test ultrasound image representation that contains a uniform background area with no target present, the region having a total area;

repeatedly dividing said total area into a selected number of blocks, each block having a pixel brightness;

calculating an average pixel brightness for each said block, wherein the averages constitute a multi-resolution scale of brightness;

calculating a ratio of the mean and standard deviation of said the average pixel brightness for each said block, wherein said ratio represents homogeneity of said each block; and calculating a weighted average of all said ratios, wherein said weighted average is said homogeneity index.

5. The method of claim 4, wherein said step of repeatedly dividing said total area into a selected number of blocks comprises repeatedly dividing said total area into blocks until a block size of one pixel is achieved.

6. The method of claim 1, wherein said image quality index is a contrast image quality index calculated by:

selecting an exact region of interest including grayscale targets;

computing a mean brightness value for each grayscale target;

selecting for each grayscale target a stored respective nominal brightness value for corresponding grayscale target associated with said optimum ultrasound image representation; and computing a total squared error of a difference between all said mean brightness values and said corresponding stored nominal values, said total squared error being the contrast image quality index.

7. The method of claim 6, wherein said step of selecting an exact region of interest comprises:

identifying center coordinates and respective radii of all grayscale targets in said optimum image representation;

translating said center coordinates and respective radii to said test image representation;

selecting an approximate region of interest of said test ultrasound image representation; and selecting at least one grayscale target center coordinate within said approximate region of interest and generating a mask based on all said selected grayscale target center coordinates and respective radii, said mask being an exact region of interest.

8. The method of claim 6, wherein said step of computing a total squared error comprises:

computing a mean brightness value for each said selected grayscale target within said exact region of interest;

computing a difference between each said mean brightness value and a respective corresponding stored nominal brightness value, wherein said respective corresponding stored nominal brightness values are obtained from said optimum image representation; and computing a total squared error of a difference between all said mean brightness values and said respective corresponding stored nominal values, said total squared error being the contrast image quality index.

9. The method of claim 1, wherein said image quality index is a signal attenuation image quality index and penetration depth image quality index calculated by:

selecting a region of the image of said test ultrasound image representation that contains a uniform background area;

calculating an average value of pixel values for at least one depth x in said region; and calculating an estimate of a signal attenuation image quality index $\lambda$ based on said average value, wherein $1/\lambda$ is the penetration depth index.

10. The method of claim 9, wherein $\lambda$ is a signal attenuation index, $I_0$ an average of pixel values for a depth x, and an intensity profile $I(x)$ is a mean pixel brightness function of x for every depth x according to the intensity profile $I(x) = I_0 e^{-\lambda x}$, said calculating an estimate of a signal attenuation index $\lambda$ comprises:

calculating an average of pixel values $I_0$ for each depth x;

performing a sequence of linear regression steps to calculate an estimate of the signal attenuation index $\lambda$, said steps including calculating $I(x) = I_0 e^{-\lambda x}$;

calculating log $I(x)$; and forming a plot of log $I(x)$ versus x and drawing a straight line having a slope through said plot of log $I(x)$ versus x, wherein a negative value of said slope is an estimate of the signal attenuation image quality index $\lambda$ and $1/\lambda$ is the penetration depth image quality index.

11. The method of claim 1, wherein said image quality index is a pin to background ratio image quality index calculated by:

selecting an exact region of the image of said test ultrasound image representation that includes evenly spaced, vertical pins imbedded at specific depths in a background gel;

calculating a first average brightest pixel value in said selected region, said first average brightest pixel value representing a pin;

calculating a second average pixel brightness value of a pixel region contiguous to said pin; and calculating a ratio of said first average brightest pixel value to said second average pixel brightness value, wherein the ratio is the pin to background ratio image quality index.

12. The method of claim 11, wherein said step of selecting an exact region of interest comprises:

identifying center coordinates and respective radii of all pin targets in said optimum image representation;

translating said center coordinates and respective radii to said test image representation;

selecting an approximate region of interest of said test ultrasound image representation; and selecting at least one pin target center coordinate within said approximate region of interest and generating a mask based on said at least one pin target center coordinate and respective radii, said mask being an exact region of interest.

13. The method of claim 1, wherein said image quality index is a resolution image quality index calculated by:

selecting a region of interest within said test ultrasound image representation that includes at least two evenly spaced pins arranged along a vertical axis and at least two evenly spaced pins arranged along a horizontal axis;

selecting brightest pixels within said region of interest, each said brightest pixel representing a respective center of a pin;

calculating a first half dimension and a first maximum dimension between adjacent pin centers arranged along a vertical axis and a second half dimension and a second maximum dimension between adjacent pin centers arranged along a horizontal axis; and calculating a first ratio of said first half width dimension to said first maximum dimension for each said adjacent pin centers arranged along a vertical axis and calculating a second ratio of said second half width dimension to said second maximum dimension for each said adjacent pin centers arranged along a horizontal axis, wherein said first ratio is a vertical component of the resolution index and said second ratio is a horizontal component of the resolution index.

14. The method of claim 1, wherein said image quality index is a geometric distortion image quality index calculated by:

selecting at least one uniform grayscale target within a region of the ultrasound test image representation;

determining a vertical and a horizontal radius for said at least one uniform grayscale target;

calculating a ratio of each said vertical radius to a respective horizontal radius; and calculating a total squared error of said ratios, said error being said geometric distortion image quality index.

15. The method of claim 14, wherein said step of selecting at least one uniform grayscale target comprises:

identifying center coordinates of all first grayscale targets in said optimum image representation;

translating all said center coordinates to corresponding second grayscale targets in said test ultrasound image representation;

selecting an approximate region of interest of said test ultrasound image representation, wherein said selected approximate region includes at least one second grayscale target, each at least one second grayscale target having a translated center coordinate; and selecting at least one second grayscale target center coordinate within said approximate region of interest.

16. The method of claim 15, wherein said step of determining a vertical and a horizontal radius comprises:

detecting changes in average pixel values in any direction from each said second grayscale target center coordinate;

selecting for each said second grayscale target a first average pixel value based on said detected changes, wherein said first average pixel value corresponds to a pixel oriented horizontally relative to said second grayscale target center coordinate and said first average pixel value represents an edge of a second grayscale target;

selecting for each said second grayscale target a second average pixel value based on said detected changes, wherein said second average pixel value corresponds to a pixel oriented vertically relative to said second grayscale target center coordinate and said second average pixel value represents an edge of a second grayscale target; and determining a horizontal radius for each said first average pixel value and determining a vertical radius for each said second average pixel value, each said radius being a distance from a corresponding center coordinate of a respective second grayscale object to a respective selected average pixel.

17. The method of claim 1, wherein said image quality index is a horizontal and a vertical linearity image quality index comprising:

selecting a region of the test ultrasound image representation that includes a representation of a set of evenly spaced pins arranged along a vertical axis and a set of evenly spaced pins arranged along a horizontal axis, each set being imbedded at a selected depth in a background gel;

determining a first set of coordinates of pins of said test ultrasound image representation;

determining a second set of coordinates of corresponding pins of said optimum image representation; and calculating a first total squared error of differences between said first and second sets of respective coordinates of pins arranged along a vertical axis, and calculating a second total squared error of differences between said first and second sets of respective coordinates of pins arranged along a horizontal axis, wherein said first and second total squared errors are the vertical linearity image quality index and horizontal linearity image quality index, respectively.

18. The method of claim 17, wherein said step of determining a first set of coordinates of pins of said test ultrasound image representation and said step of determining a second set of coordinates of corresponding pins of said optimum image representation comprises:

selecting first brightest pixel values in said selected region, each said first brightest pixel value representing a center of a respective pin;

determining a first set of coordinates corresponding to each said first brightest pixel values, said first set being determined separately for said pins arranged along a horizontal axis and for said pins arranged along a vertical axis; and determining a second set of coordinates of second brightest pixel values from said optimum image representation, said second brightest pixel values corresponding to said first brightest pixel values, said second set being determined separately for said pins arranged along a horizontal axis and for said pins arranged along a vertical axis.

19. The method of claim 1, wherein said image health quality index is obtained by arithmetically combining at least two of said image quality indices, wherein said image quality indices include said homogeneity index, said contrast index, said signal attenuation and penetration depth index, said pin to background ratio index, said resolution index, said linearity index, and said geometric distortion index.

20. The method of claim 19, wherein said step of arithmetically combining comprises determining the Health Quality Index by performing the following calculation $$\sqrt{\frac{(x_1 - \mu_1)^2}{\sigma_1^2} + \dots + \frac{(x_n - \mu_n)^2}{\sigma_n^2}}$$

wherein $x_1 \ldots x_n$ are values of respective image quality indices calculated for a test ultrasonic image representation, $\mu_1 \ldots \mu_n$ are values of respective image quality indices calculated for an optimum image representation, and $\sigma_1 \ldots \sigma_n$ are standard deviations of the $x_1 \ldots x_n$ values.

21. A system for quantitatively evaluating image quality characteristics of an ultrasound imaging machine comprising:

a control circuit including a storage memory for data storage;

a standard phantom;

a system control program included in said control circuit for controlling an optimum ultrasound image representation of said phantom and a test ultrasound image representation of said phantom, said test ultrasound image representation being obtained from an ultrasound instrument under test, wherein one or more image quality parameters to be calculated and one or more regions of interest of the test ultrasound image representation are selected, each of said one or more regions of interest corresponding to an image quality parameter to be tested;

the system control program automatically shifting in memory the test ultrasound image representation until said representation is in registration with said optimum ultrasound image representation, the system control program calculating respective image quality indices for each said selected one or more regions of interest, and further calculating an image health index from said respective image quality indices, said image health index quantitatively representing image quality characteristics of an ultrasound imaging machine.

22. The system of claim 21, wherein said system control program automatically shifts in memory the test ultrasound image representation until said representation is in registration with said optimum ultrasound image representation by calculating a cross-correlation coefficient, said cross-correlation coefficient representing a quantitative degree of proximity of said test ultrasound image representation relative to said optimum image registration and is given by $$C = \frac{\sum_{i,j} I_1(i, j) I_2(i, j)}{\sqrt{\sum_{i,j} I_1^2(i, j) \sum_{i,j} I_2^2(i, j)}}$$

wherein C equals the cross-correlation coefficient; $I_1(i,j)$ equals test image pixel locations, and $I_2(i,j)$ equals optimum image pixel locations.

23. The system of claim 22, wherein said system control program calculates said image health quality index by causing at least two of said image quality indices to be arithmetically combined in said control, wherein said image quality indices include a homogeneity index, a contrast index, a signal attenuation and penetration depth index, a pin to background ratio index, a resolution index, a linearity index, and a geometric distortion index.

24. The system of claim 23, wherein said system control program (101) causes said image health quality index to be calculated by said control circuit by performing the following calculation $$\sqrt{\frac{(x_1 - \mu_1)^2}{\sigma_1^2} + \dots + \frac{(x_n - \mu_n)^2}{\sigma_n^2}}$$

wherein $x_1 \ldots x_n$ are values of respective image quality indices calculated for a test ultrasonic image representation, $\mu_1 \ldots \mu_n$ are values of respective image quality indices calculated for an optimum image representation, and $\sigma_1 \ldots \sigma_n$ are standard deviations of the $x_1 \ldots x_n$ values.

* * * * *